(12) United States Patent
Logan

(10) Patent No.: US 7,722,822 B2
(45) Date of Patent: May 25, 2010

(54) SAMPLE TUBE AND VIAL PROCESSING SYSTEM, AND METHOD FOR PROCESSING THE SAMPLE

(75) Inventor: Thomas Michael Logan, Newton Square, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 588 days.

(21) Appl. No.: 11/388,312

(22) Filed: Mar. 23, 2006

(65) Prior Publication Data

US 2007/0224089 A1 Sep. 27, 2007

(51) Int. Cl.
*B01L 3/00* (2006.01)

(52) U.S. Cl. ............... 422/102; 422/939; 422/940; 422/941; 422/942; 422/943; 422/944; 422/945; 422/946; 206/430; 222/501

(58) Field of Classification Search ......... 422/939–949, 422/102; 222/568–570; 141/98, 319; 206/430
See application file for complete search history.

(56) References Cited

U.S. PATENT DOCUMENTS

| | | | | | |
|---|---|---|---|---|---|
| 3,917,063 | A | * | 11/1975 | Chibret et al. | 206/221 |
| 3,945,617 | A | * | 3/1976 | Callery | 366/347 |
| 4,573,506 | A | * | 3/1986 | Paoletti | 141/98 |
| 4,986,322 | A | * | 1/1991 | Chibret et al. | 141/319 |
| 5,066,463 | A | * | 11/1991 | Chang | 422/56 |
| 5,167,929 | A | * | 12/1992 | Korf et al. | 422/102 |
| 5,702,019 | A | * | 12/1997 | Grimard | 215/301 |
| 5,874,048 | A | * | 2/1999 | Seto et al. | 422/100 |
| 5,971,181 | A | * | 10/1999 | Niedospial et al. | 215/247 |
| 6,686,204 | B2 | * | 2/2004 | Dubrowny et al. | 436/69 |
| 6,779,566 | B2 | * | 8/2004 | Engel | 141/25 |
| 6,808,933 | B1 | | 10/2004 | Prest | |
| 6,861,259 | B2 | * | 3/2005 | Columbus | 436/3 |
| 7,011,794 | B2 | * | 3/2006 | Kagan et al. | 422/102 |
| 7,338,634 | B2 | * | 3/2008 | Chang | 422/56 |
| 2006/0063268 | A1 | | 3/2006 | Prest | |

* cited by examiner

*Primary Examiner*—Jill Warden
*Assistant Examiner*—Shogo Sasaki

(57) ABSTRACT

An apparatus for processing an analyte includes a first receptacle having a first aperture, the first aperture having a first configuration; and a second receptacle having a second aperture, the second aperture having a second configuration. The first configuration and the second configuration are complementary, such that the first and second apertures engage each other at a sealing surface, whereby analyte solution within the first receptacle passes into the second receptacle substantially without leaking at the engaged first and second apertures. A method for processing an analyte comprises engaging the first and second receptacles at the sealing surface; putting a first batch of analyte solution into the first receptacle, processing the analyte solution; transferring the processed analyte solution into the second receptacle, and disengaging the second receptacle from the first receptacle.

7 Claims, 3 Drawing Sheets

SAMPLE TUBE AND VIAL PROCESSING SYSTEM, AND METHOD FOR PROCESSING THE SAMPLE

BACKGROUND AND SUMMARY

The invention relates to the field of chemical analysis, particularly identification of analyte substances within samples such as liquid samples.

Techniques have been developed for the analysis, or detection of the presence, of substances, such as organic compounds, within samples such as samples of biological fluids. For instance, samples of human blood, saliva, urine, etc., can be tested for the presence of drugs of abuse. In many cases, the substances to be detected may be present in small quantities, or at low concentrations, within the sample.

Although analytical instrumentation is becoming increasingly sensitive, and analyte detection continues to improve, chemical analytes in solution sometimes must be concentrated, prior to chemical analysis. Typically, such concentration is done using bench-top chemical processes specifically developed or tailored to the analytical problem at hand. Such processes include, for instance, solvent condensation or evaporation techniques that eliminate the solvent while retaining the analyte, by exploiting differences in physical properties such as volatility.

In gas chromatography (GC), large volume injection techniques have been developed with special hardware, such as pre-column inlets, to allow more sensitive detection by evaporation of solvent, while attempting to retain analyte inside the pre-column inlets prior to the analyte being delivered to the analytical column for chromatographic separation and analysis/detection.

For the testing process, the samples are handled in vials, test tubes, etc. Loss or contamination of the sample should be eliminated or kept to a minimum, and the equipment for handling the samples is designed with that in mind.

In one example of a testing scenario, a relatively large (for instance, greater than 2 ml) sample volume is to be processed by condensation to a smaller volume (for instance, less than 1 ml) prior to injection into instrumentation such as gas chromatography or liquid chromatography equipment. Condensation may be done by heating the sample, exposing the sample to a stream of gas to facilitate evaporation of volatile solvent, or some combination of these or other techniques.

Such condensation improves detection limits, by enabling a larger fraction of the total sample to be analyzed. However, the condensation requires the sample, which initially is in a larger volume container, to be transferred to a smaller volume container, such as a standard chromatography vial, or a vial with an integrated insert. These vials typically have volumes less than 2 ml, and fit inside standard automated liquid sampler systems.

In co-pending U.S. patent application Ser. No. 10/947844, Prest, "Method and Article for Analyte Concentration Free of Immediate Transfer," there is described a method and apparatus for concentrating an analyte directly into a test receptacle. A liquid containing an analyte is placed into a first receptacle, which is in direct fluid communication with a second receptacle. The analyte is concentrated, into the second receptacle, by known processes. The second receptacle is then used, to provide the concentrated analyte to an instrument for analysis, without liquid transfer and without loss of analyte.

However, the volume of analyte injected is usually small. As a consequence, repetitive (manual or automated) transfers and condensation steps are required to complete the transfer of the larger volume. Each of these transfer steps is subject to possible loss, and the total transfer process therefore is labor intensive. Also, rinses of the original sample container are required to minimize losses on the surfaces. This process is itself frequently subject to losses, and so is seldom fully quantitative.

There is provided an apparatus for concentrating an analyte, comprising a first receptacle having a first aperture, the first aperture having a first configuration; and a second receptacle having a second aperture, the second aperture having a second configuration. The first configuration and the second configuration are complementary, such that the first and second apertures engage each other at a sealing surface. Analyte solution within the first receptacle passes into the second receptacle substantially without leaking at the engaged first and second apertures.

Further features and advantages of the present invention, as well as the structure and operation of preferred embodiments of the present invention, are described in detail below with reference to the accompanying exemplary drawings.

DETAILED DESCRIPTION

Figure 1:
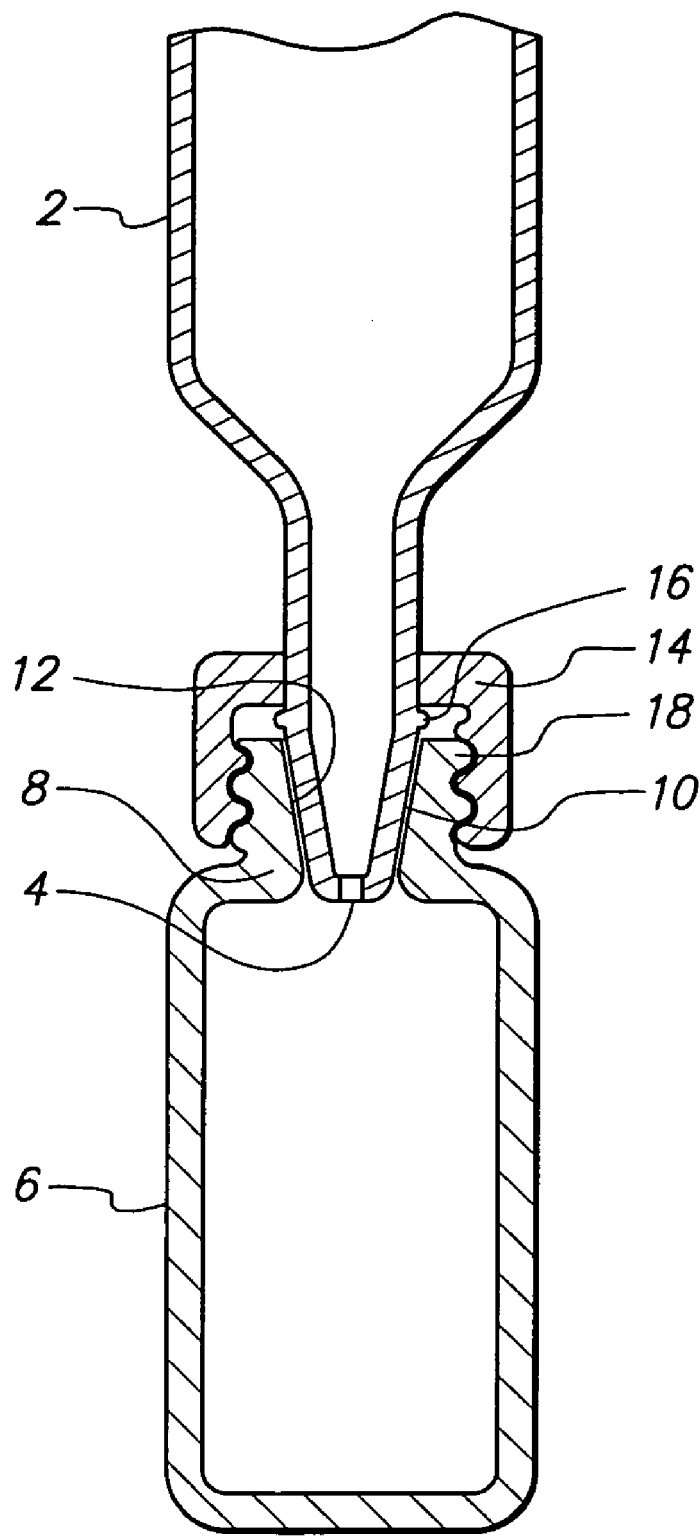
FIG. 1 is a cross-sectional view of an apparatus according to an embodiment of the invention.

FIG. 1 is a cross-sectional diagram of a sample concentration tube and vial system, according to an embodiment of the invention. The system and method of the invention may be used, for instance, to condense or otherwise concentrate a sample such as an analyte solution. One reason for doing so, for instance, is to facilitate testing of the sample for the presence or quantity of an analyte in solution.

A first receptacle 2 contains a sample, such as a quantity of the analyte solution, which is to be processed for such testing, or for other appropriate use. The first receptacle 2 can be a known container or vessel, such as a modified test tube, rotary evaporator flask, Kuderna Danish concentrator tube, etc. The first receptacle 2 serves, for instance, as a concentration tube, where processing of the sample is to include concentration of the sample by means of heating, solvent evaporation, etc.

The sample may be put into the first receptacle 2 through a first opening (not shown). The sample exits through a second opening 4.

A second receptacle 6 can be a known chromatography vial, with or without an integrated insert. The second receptacle 6 may be suitable for coupling to a tester which will test, for instance, for the analyte within the processed sample. The second receptacle 6 has an opening 8, for receiving a sample.

The first receptacle 2 includes a first configuration, for instance a taper 10 at its second opening 4. The second receptacle 6 likewise has a second configuration, for instance a taper 12 at an inner dimension of the opening 8.

The first and second configurations of the respective first and second receptacles 2 and 6 are complementary, so as to enable the first receptacle 2 and the second receptacle 6 to engage each other at their respective first and second configurations. For instance, in the embodiment of FIG. 1, the taper 10 and the taper 12 match each other. Because the tapers 10 and 12 are complementary by matching each other, when the first and second receptacles 2 and 6 are engaged as shown, the respective first and second configurations form a sealing surface, which substantially prevents leakage of sample.

While the first and second configurations are shown as the matching tapers 10 and 12, various alternative types of complementary configurations are possible. For instance, the complementary configurations might engage each other by means of friction, to hold the first and second receptacles 2 and 6 together after they are engaged with each other. Alternatively, the first and second configurations might include respective engaging structures, such as matching threads on cylindrical portions of suitably complementary inner and outer diameters of the second opening 4 and the opening 8.

Referring again to FIG. 1, the illustrated embodiment includes a locking member, shown as a locking cap 14, which is integral with the first receptacle 2, held in place by a first locking structure such as a locking member restraint structure such as a small nub, here shown as a nub 16.

Also, the second receptacle 6 includes a second locking structure, shown as screw threads 18. When the second receptacle 6 is positioned to engage the first receptacle 2, the locking cap 14 is screwed on, so as to engage the screw threads 18. Likewise, the locking cap 14 is unscrewed, to disengage from the screw threads 18.

Figure 2:
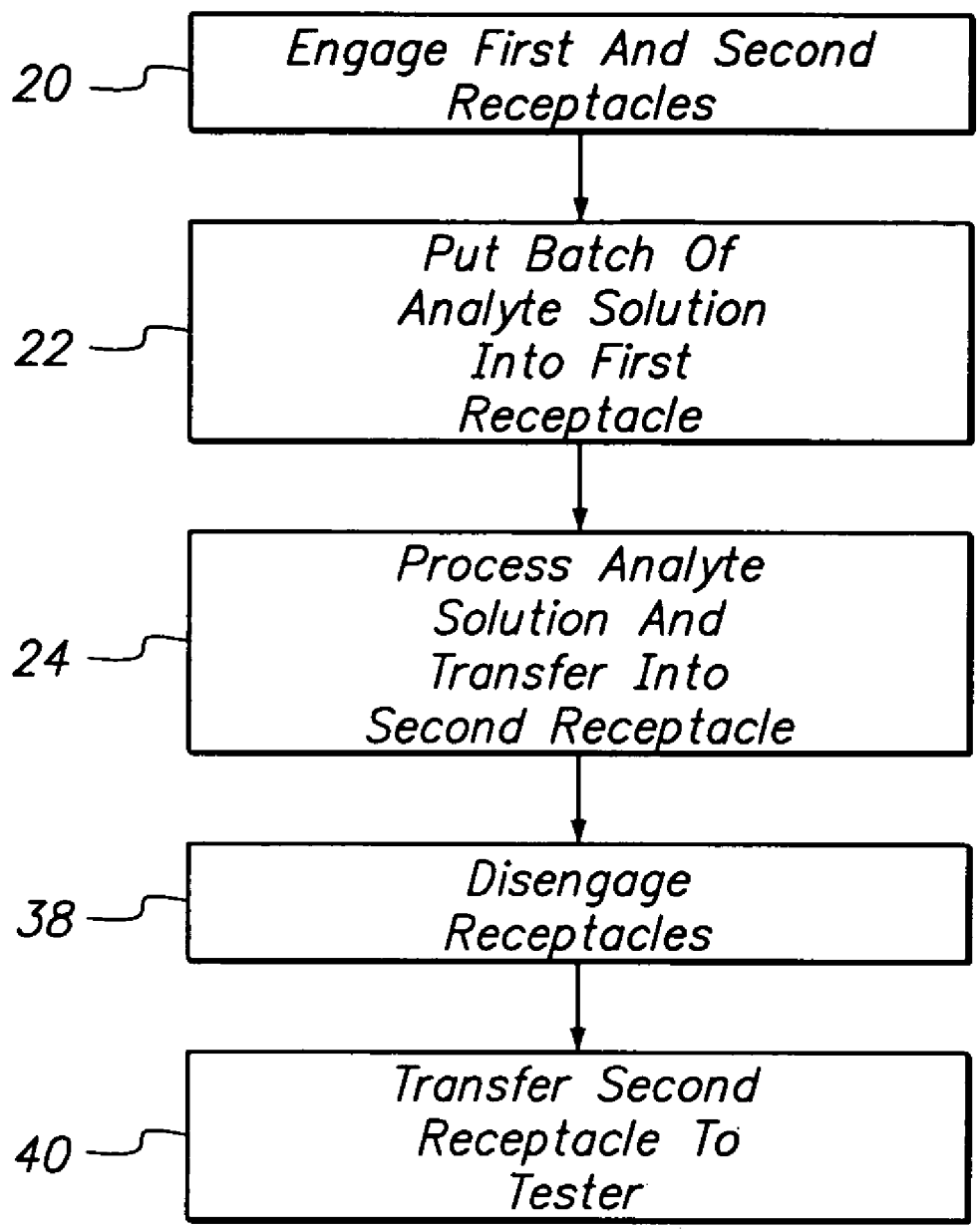
FIGS. 2 and 3 are flowcharts describing a method according to an embodiment of the invention.

FIG. 2 is a flowchart, showing a method for processing a sample such as an analyte solution, using a structure such as that shown in FIG. 1.

The first receptacle 2 and the second receptacle 6 are engaged (20). An analyte solution is put into the first receptacle 2 (22).

Figure 3:
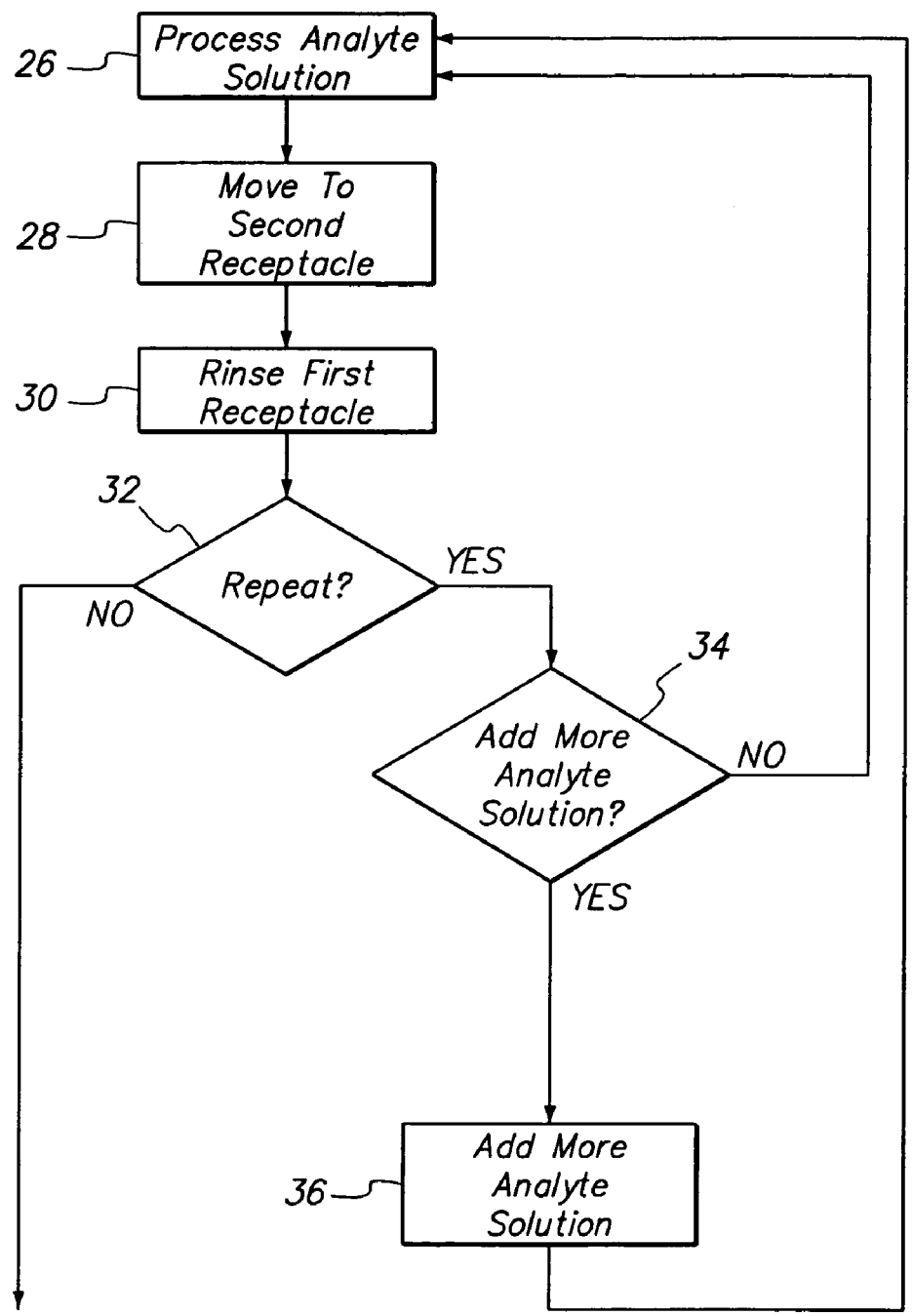

The analyte solution is then processed (24), in a manner suitable for the user. Further exemplary details are given in connection with FIG. 3, which is a more detailed flowchart illustrating an embodiment of the processing (24).

For instance, the user may want to process the analyte solution (26) by condensing or concentrating the analyte solution to increase the concentration of analyte within the solution.

Analyte solution in the first receptacle 2 is processed (for instance, condensed) directly (28) into the second receptacle 6. It is a noteworthy feature of the invention that, by so doing, no additional transfer of the analyte solution to yet another receptacle is necessary. Rather, the processed analyte solution in the second receptacle 6 may be provided directly to the tester, without transfers.

To avoid losing analyte because of sample "sticking" to the sides, i.e., due to surface tension, residue adhesion, etc., in one embodiment the interior surface of the first receptacle 2 is rinsed (30) using a substance such as the solvent of the analyte solution. Such rinses of the walls of the first receptacle 2 automatically descend into the second receptacle 6.

In another embodiment of the system of the invention, the interior wall of the first receptacle 2 is treated with a deactivation process, to reduce the loss of analyte due to such sample "sticking" to the interior wall. While the discussion which follows will focus on first receptacle 2, the second receptacle 6 can likewise be treated.

For instance, for the deactivation process, the first receptacle 2 can be coated with any of a variety of materials, such as silicon or siloxane materials. For example, if the first receptacle 2 is made of glass, its interior surface can be coated with a silicon material, such as silicon carbide or silicon oxide, or with a siloxane, such as a polymeric siloxane. Suitable polymeric siloxanes include polymethylhydrosiloxane.

Any of a variety of known methods can be employed for applying the silicon or siloxane material to the interior surface of the first receptacle 2. All or a portion of the interior surfaces can be coated with a material, such as a silicon or siloxane material. In an embodiment, the portion of the interior surface of the each receptacle that contacts, or that can contact, a fluid during operation can be coated with the material, such as a silicon or siloxane material.

In order to ensure that the method produces a sufficient quantity of processed analyte solution, the processing (26) may be repeated. This may be desirable, for instance, if the rinsing (30) has diluted the processed sample with extra solvent. In such case a suitable choice, or test, is made (32). If it is so decided, the processing (26), etc., are repeated and the sample is further processed; for instance, condensed further, down to an appropriate volume.

Also, it may be the case that processing one batch of sample is not sufficient to product a desired quantity of processed analyte solution. In such case, it may be desired to process a first batch of analyte solution into the second receptacle 6 as described above, and then put an additional batch of sample into the first receptacle 2 and repeat the process. Thus, in another embodiment the method can include testing (34) to determine whether an additional batch of sample is needed to produce a sufficient quantity of processed sample, and if so, adding more sample (36) and repeating.

Referring back to FIG. 2, once the processing (24) has been done, the first receptacle 2 and the second receptacle 6 are separated by disengaging them from each other (38), for instance by unscrewing the locking cap 14.

Then, the disengaged second receptacle 6, containing the processed sample, may be carried or otherwise transported (40) to a test unit, such as an I-AS Integrated Autosampler made by Agilent Technologies, Inc. For this transport, a standard screw cap may be installed on the second receptacle 6. The second receptacle 6 is installed into the test unit, in a manner suitable for the test unit being employed. The test unit then analyses the processed analyte solution. Details of the installation on the test unit, and the analysis, are up to the discretion of the user.

Although the present invention has been described in detail with reference to particular embodiments, persons possessing ordinary skill in the art to which this invention pertains will appreciate that various modifications and enhancements may be made without departing from the spirit and scope of the claims that follow.

What is claimed is:

1. An apparatus for processing an analyte, comprising:
  a first receptacle having i) a first aperture, ii) an exterior surface having a first configuration, the first configuration adjacent the first aperture, and iii) a first locking structure integral with the exterior surface of the first receptacle;
  a locking member retained on the first receptacle by the first locking structure; and
  a second receptacle having i) a second aperture, ii) an interior surface having a second configuration, the second configuration adjacent the second aperture, and iii) a second locking structure integral with the exterior surface of the second receptacle;
  wherein the first configuration and the second configuration are complementary and form a sealing surface interior to the second receptacle when the first and second receptacles are engaged, whereby the sealing surface provides for analyte solution within the first receptacle passing into the second receptacle via the first and second apertures, substantially without leaking; and
  wherein, when the first and second receptacles are engaged, the locking member is disposed at the first and second locking structures and is operable to engage the first and second locking structures.

2. An apparatus as recited in claim 1, wherein:
the first configuration includes a first taper; and
the second configuration includes a second taper that matches the first taper.

3. An apparatus as recited in claim 1, wherein:
the second locking structure includes screw threads.

4. An apparatus as recited in claim 3, wherein the locking member includes a screw cap.

5. An apparatus as recited in claim 1, wherein:
the first receptacle has an interior surface coated with a material that reduces loss of analyte due to the analyte sticking to the interior surface of the first receptacle.

6. An apparatus as recited in claim 5, wherein the material coating the interior surface of the first receptacle is selected from the group consisting of: (i) silicon, (ii) siloxane material, (iii) silicon carbide, (iv) silicon oxide, (v) polymeric siloxane, and (vi) polymethylhydrosiloxane.

7. An apparatus as recited in claim 1, wherein the first locking structure is a nub which is integral with the first receptacle.

* * * * *